United States Patent
Hartwell et al.

(10) Patent No.: US 12,005,181 B2
(45) Date of Patent: Jun. 11, 2024

(54) PRESSURE WOUND THERAPY STATUS INDICATION VIA EXTERNAL DEVICE

(71) Applicant: Smith & Nephew PLC, Watford (GB)

(72) Inventors: Edward Yerbury Hartwell, Hull (GB); Damian Smith, Hull (GB)

(73) Assignee: Smith & Nephew PLC, Watford (GB)

( * ) Notice: Subject to any disclaimer, the term of this patent is extended or adjusted under 35 U.S.C. 154(b) by 443 days.

(21) Appl. No.: 16/468,645

(22) PCT Filed: Dec. 8, 2017

(86) PCT No.: PCT/EP2017/081959
§ 371 (c)(1),
(2) Date: Jun. 11, 2019

(87) PCT Pub. No.: WO2018/108724
PCT Pub. Date: Jun. 21, 2018

(65) Prior Publication Data
US 2019/0282738 A1    Sep. 19, 2019

Related U.S. Application Data

(60) Provisional application No. 62/464,173, filed on Feb. 27, 2017, provisional application No. 62/433,179, filed on Dec. 12, 2016.

(51) Int. Cl.
*A61M 1/00* (2006.01)

(52) U.S. Cl.
CPC .............. *A61M 1/918* (2021.05); *A61M 1/96* (2021.05); *A61M 1/962* (2021.05); *A61M 1/985* (2021.05);
(Continued)

(58) Field of Classification Search
CPC .................... A61M 1/962; A61M 1/90; A61M 2205/3584; A61M 2205/502; A61M 2205/52; A61M 2209/088
See application file for complete search history.

(56) References Cited

U.S. PATENT DOCUMENTS

| | | |
|---|---|---|
| 3,874,387 A | 4/1975 | Barbieri |
| 4,224,941 A | 9/1980 | Stivala |
| | (Continued) | |

FOREIGN PATENT DOCUMENTS

| | | |
|---|---|---|
| CN | 201664463 U | 12/2010 |
| DE | 19844355 A1 | 4/2000 |
| | (Continued) | |

OTHER PUBLICATIONS

Invitation to Pay Additional Fees And, Where Applicable, Protest Fee, re PCT Application No. PCT/EP2017/081959, mailed Mar. 13, 2018.

(Continued)

*Primary Examiner* — Benjamin J Klein
*Assistant Examiner* — Hans Kaliher
(74) *Attorney, Agent, or Firm* — Knobbe, Martens, Olson & Bear, LLP

(57) ABSTRACT

According to certain aspects, a negative pressure wound therapy system can include a negative pressure therapy apparatus configured to apply negative pressure to a wound of a patient. The negative pressure therapy device can include a wound dressing configured to be placed over the wound, a negative pressure source supported by the wound dressing, and a controller. The controller can include a processor configured to determine operating data of the negative pressure therapy apparatus and transmit the operating data. The negative pressure wound therapy system can further include a wireless communication device having a controller with one or more processors. The controller of the wireless communication device can be configured to be communicatively coupled to the negative pressure therapy apparatus and further configured to receive the operating data transmitted by the controller of the negative pressure (Continued)

therapy apparatus. The controller can be further configured to output the operating data.

15 Claims, 5 Drawing Sheets

(52) U.S. Cl.
CPC .............. *A61M 2205/3584* (2013.01); *A61M 2205/3592* (2013.01); *A61M 2205/502* (2013.01); *A61M 2205/52* (2013.01); *A61M 2209/088* (2013.01); *A61M 2210/086* (2013.01)

(56) References Cited

U.S. PATENT DOCUMENTS

| | | |
|---|---|---|
| 4,398,910 A | 8/1983 | Blake et al. |
| 4,534,356 A | 8/1985 | Papadakis |
| 4,569,674 A | 2/1986 | Phillips et al. |
| 4,624,656 A | 11/1986 | Clark et al. |
| 4,681,562 A | 7/1987 | Beck et al. |
| 4,767,943 A | 8/1988 | Adler et al. |
| 4,979,944 A | 12/1990 | Luzsicza |
| 5,055,195 A | 10/1991 | Trasch et al. |
| 5,055,198 A | 10/1991 | Shettigar |
| 5,056,510 A | 10/1991 | Gilman |
| 5,152,757 A | 10/1992 | Eriksson |
| 5,181,905 A | 1/1993 | Flam |
| 5,266,928 A | 11/1993 | Johnson |
| D357,743 S | 4/1995 | Bilitz et al. |
| 5,527,293 A | 6/1996 | Zamierowski |
| 5,549,584 A | 8/1996 | Gross |
| 5,643,189 A | 7/1997 | Masini |
| 5,779,657 A | 7/1998 | Daneshvar |
| 5,833,646 A | 11/1998 | Masini |
| 5,902,256 A | 5/1999 | Benaron |
| 5,964,723 A | 10/1999 | Augustine |
| 6,071,267 A | 6/2000 | Zamierowski |
| 6,142,982 A | 11/2000 | Hunt et al. |
| 6,168,800 B1 | 1/2001 | Dobos et al. |
| 6,183,438 B1 | 2/2001 | Berguer |
| 6,225,523 B1 | 5/2001 | Masini |
| 6,261,276 B1 | 7/2001 | Reitsma |
| 6,261,283 B1 | 7/2001 | Morgan et al. |
| 6,398,767 B1 | 6/2002 | Fleischmann |
| 6,458,109 B1 | 10/2002 | Henley et al. |
| 6,471,982 B1 | 10/2002 | Lydon et al. |
| 6,589,229 B1 | 7/2003 | Connelly et al. |
| 6,599,262 B1 | 7/2003 | Masini |
| 6,607,495 B1 | 8/2003 | Skalak et al. |
| 6,685,681 B2 | 2/2004 | Lockwood et al. |
| 6,787,682 B2 | 9/2004 | Gilman |
| 6,794,554 B2 | 9/2004 | Sessions et al. |
| 6,800,074 B2 | 10/2004 | Henley et al. |
| 6,855,135 B2 | 2/2005 | Lockwood et al. |
| 6,942,633 B2 | 9/2005 | Odland |
| 6,951,553 B2 | 10/2005 | Bubb et al. |
| 6,979,324 B2 | 12/2005 | Bybordi et al. |
| 7,004,915 B2 | 2/2006 | Boynton et al. |
| 7,022,113 B2 | 4/2006 | Lockwood et al. |
| 7,067,709 B2 | 6/2006 | Murata et al. |
| 7,070,584 B2 | 7/2006 | Johnson et al. |
| 7,087,806 B2 | 8/2006 | Scheinberg et al. |
| 7,108,683 B2 | 9/2006 | Zamierowski |
| 7,216,651 B2 | 5/2007 | Argenta et al. |
| 7,338,482 B2 | 3/2008 | Lockwood et al. |
| 7,361,184 B2 | 4/2008 | Joshi |
| 7,524,315 B2 | 4/2009 | Blott et al. |
| 7,553,306 B1 | 6/2009 | Hunt et al. |
| 7,611,500 B1 | 11/2009 | Lina et al. |
| 7,615,036 B2 | 11/2009 | Joshi et al. |
| D605,775 S | 12/2009 | Koch et al. |
| D608,007 S | 1/2010 | Arbesman et al. |
| 7,645,253 B2 | 1/2010 | Gura et al. |
| 7,687,678 B2 | 3/2010 | Jacobs |
| 7,776,028 B2 | 8/2010 | Miller et al. |
| D625,422 S | 10/2010 | Arbesman et al. |
| 7,815,616 B2 | 10/2010 | Boehringer et al. |
| 7,837,673 B2 | 11/2010 | Vogel |
| 7,896,864 B2 | 3/2011 | Lockwood et al. |
| 7,922,676 B2 | 4/2011 | Daskal et al. |
| 7,922,703 B2 | 4/2011 | Riesinger |
| 7,942,866 B2 | 5/2011 | Radl et al. |
| 7,959,624 B2 | 6/2011 | Riesinger |
| 7,976,519 B2 | 7/2011 | Bubb et al. |
| 8,007,257 B2 | 8/2011 | Heaton et al. |
| 8,007,481 B2 | 8/2011 | Schuessler et al. |
| 8,062,272 B2 | 11/2011 | Weston |
| 8,092,441 B2 | 1/2012 | Sugito |
| 8,158,844 B2 | 4/2012 | McNeil |
| 8,167,869 B2 | 5/2012 | Wudyka |
| 8,200,223 B2 * | 6/2012 | Harada ................. H04W 36/02 709/201 |
| 8,212,100 B2 | 7/2012 | Moore |
| 8,215,929 B2 | 7/2012 | Shen et al. |
| 8,323,264 B2 | 12/2012 | Weston et al. |
| 8,371,829 B2 | 2/2013 | Jaeb et al. |
| 8,404,921 B2 | 3/2013 | Lee et al. |
| 8,409,160 B2 | 4/2013 | Locke et al. |
| 8,419,696 B2 | 4/2013 | Wilkes |
| 8,425,478 B2 | 4/2013 | Olson |
| 8,439,894 B1 | 5/2013 | Miller |
| 8,449,508 B2 | 5/2013 | Coulthard et al. |
| 8,500,776 B2 | 8/2013 | Ebner |
| 8,529,548 B2 | 9/2013 | Blott et al. |
| 8,545,466 B2 | 10/2013 | Andresen et al. |
| 8,569,566 B2 | 10/2013 | Blott et al. |
| 8,603,074 B2 | 12/2013 | Kagan |
| 8,641,691 B2 | 2/2014 | Fink et al. |
| 8,641,693 B2 | 2/2014 | Locke et al. |
| 8,702,665 B2 | 4/2014 | Locke et al. |
| 8,795,257 B2 | 8/2014 | Coulthard et al. |
| 8,814,842 B2 | 8/2014 | Coulthard et al. |
| 8,821,458 B2 | 9/2014 | Locke et al. |
| 8,834,452 B2 | 9/2014 | Hudspeth et al. |
| 8,870,837 B2 | 10/2014 | Locke et al. |
| 8,961,496 B2 | 2/2015 | Locke et al. |
| 8,974,429 B2 | 3/2015 | Gordon et al. |
| 9,061,095 B2 | 6/2015 | Adie et al. |
| 9,084,845 B2 | 7/2015 | Adie et al. |
| 9,089,630 B2 | 7/2015 | Perkins et al. |
| 9,198,802 B2 | 12/2015 | Robinson et al. |
| 9,211,365 B2 | 12/2015 | Weston |
| 9,259,558 B2 | 2/2016 | Tsai |
| 9,265,665 B2 | 2/2016 | Robinson et al. |
| 9,265,867 B2 | 2/2016 | Coulthard et al. |
| 9,283,118 B2 | 3/2016 | Locke et al. |
| 9,393,354 B2 | 7/2016 | Freedman et al. |
| 9,414,968 B2 | 8/2016 | Heagle |
| 9,421,133 B2 | 8/2016 | Hu et al. |
| 9,427,505 B2 | 8/2016 | Askem et al. |
| 9,446,176 B2 | 9/2016 | Locke et al. |
| 9,452,088 B2 | 9/2016 | Shulman et al. |
| 9,452,245 B2 | 9/2016 | Jaeb et al. |
| 9,456,928 B2 | 10/2016 | Haggstrom et al. |
| 9,560,975 B2 | 2/2017 | Mei et al. |
| D787,690 S | 5/2017 | Mackay et al. |
| 9,770,368 B2 | 9/2017 | Robinson et al. |
| 9,795,725 B2 | 10/2017 | Joshi et al. |
| 9,814,811 B2 | 11/2017 | Aalders et al. |
| 9,907,703 B2 | 3/2018 | Allen et al. |
| 9,925,092 B2 | 3/2018 | Luckemeyer et al. |
| RE46,778 E | 4/2018 | Peron |
| 9,956,120 B2 | 5/2018 | Locke |
| 10,004,914 B2 | 6/2018 | Nettesheim et al. |
| 10,010,656 B2 | 7/2018 | Jaeb et al. |
| 10,016,309 B2 | 7/2018 | Hartwell |
| 10,016,544 B2 | 7/2018 | Coulthard et al. |
| 10,046,095 B1 | 8/2018 | Middaugh et al. |
| 10,086,117 B2 | 10/2018 | Locke et al. |
| 10,123,909 B2 | 11/2018 | Hartwell |
| 10,384,041 B2 | 8/2019 | Patel et al. |
| 10,660,994 B2 | 5/2020 | Askem et al. |

(56) References Cited

U.S. PATENT DOCUMENTS

| | | |
|---|---|---|
| 2003/0135388 A1* | 7/2003 | Martucci .............. G06Q 10/087 705/2 |
| 2003/0212357 A1 | 11/2003 | Pace |
| 2004/0076662 A1 | 4/2004 | Riesinger |
| 2004/0087884 A1 | 5/2004 | Haddock et al. |
| 2004/0167482 A1 | 8/2004 | Watson |
| 2005/0012616 A1 | 1/2005 | Forster et al. |
| 2005/0045461 A1 | 3/2005 | Sweetland et al. |
| 2005/0065471 A1 | 3/2005 | Kuntz |
| 2005/0119737 A1 | 6/2005 | Bene et al. |
| 2005/0137539 A1 | 6/2005 | Biggie et al. |
| 2006/0029650 A1 | 2/2006 | Coffey |
| 2006/0086598 A1 | 4/2006 | Sneek et al. |
| 2006/0107642 A1 | 5/2006 | Smith et al. |
| 2006/0259102 A1 | 11/2006 | Slatkine |
| 2007/0093786 A1* | 4/2007 | Goldsmith ......... A61B 5/14532 604/890.1 |
| 2007/0128055 A1 | 6/2007 | Lee |
| 2007/0179460 A1 | 8/2007 | Adahan |
| 2007/0225663 A1 | 9/2007 | Watt et al. |
| 2007/0255187 A1 | 11/2007 | Branch |
| 2007/0265586 A1* | 11/2007 | Joshi .................. A61F 13/0213 604/313 |
| 2008/0021356 A1 | 1/2008 | Castello Escude et al. |
| 2008/0051716 A1 | 2/2008 | Stutz |
| 2009/0012484 A1 | 1/2009 | Nielsen et al. |
| 2009/0048556 A1 | 2/2009 | Durand |
| 2010/0022990 A1 | 1/2010 | Karpowicz et al. |
| 2010/0100160 A1 | 4/2010 | Edman et al. |
| 2010/0137775 A1 | 6/2010 | Hu et al. |
| 2010/0160881 A1 | 6/2010 | Lin et al. |
| 2010/0280469 A1 | 11/2010 | Hall et al. |
| 2010/0292632 A1 | 11/2010 | Mulvihill et al. |
| 2011/0006876 A1 | 1/2011 | Moberg et al. |
| 2011/0092927 A1 | 4/2011 | Wilkes et al. |
| 2011/0224631 A1 | 9/2011 | Simmons et al. |
| 2011/0292623 A1 | 12/2011 | Stanley |
| 2011/0305736 A1 | 12/2011 | Wieland et al. |
| 2012/0059294 A1 | 3/2012 | Schubert et al. |
| 2012/0109034 A1 | 5/2012 | Locke et al. |
| 2013/0215638 A1 | 8/2013 | Dabov et al. |
| 2013/0274629 A1* | 10/2013 | Duesterhoft ............. H04Q 9/00 600/573 |
| 2014/0018637 A1* | 1/2014 | Bennett ................... G16Z 99/00 607/51 |
| 2014/0100536 A1 | 4/2014 | Angel |
| 2014/0343518 A1 | 11/2014 | Riesinger |
| 2015/0025482 A1* | 1/2015 | Begin ................. A61M 1/0001 604/318 |
| 2015/0057625 A1 | 2/2015 | Coulthard |
| 2015/0133829 A1* | 5/2015 | DeBusk ............ A61F 13/00068 601/6 |
| 2015/0202354 A1 | 7/2015 | Wall |
| 2015/0250931 A1 | 9/2015 | Bharti et al. |
| 2016/0015873 A1 | 1/2016 | Robinson et al. |
| 2016/0166438 A1 | 6/2016 | Rovaniemi |
| 2016/0199546 A1 | 7/2016 | Chao |
| 2016/0242964 A1 | 8/2016 | Rapp et al. |
| 2016/0271305 A1 | 9/2016 | Kurihara et al. |
| 2016/0361473 A1 | 12/2016 | Robinson et al. |
| 2017/0112974 A1 | 4/2017 | Fujisaki |
| 2017/0112975 A1 | 4/2017 | Fujisaki |
| 2017/0127525 A1 | 5/2017 | Schonholz |
| 2017/0232189 A1 | 8/2017 | Qin et al. |
| 2017/0296714 A1 | 10/2017 | Locke et al. |
| 2017/0319761 A1 | 11/2017 | Locke et al. |
| 2017/0326277 A1 | 11/2017 | Huang |
| 2017/0347940 A1* | 12/2017 | Carr ...................... A61B 5/4842 |
| 2017/0368239 A1 | 12/2017 | Askem et al. |
| 2018/0008760 A1 | 1/2018 | Zilbershlag et al. |
| 2018/0021178 A1 | 1/2018 | Locke et al. |
| 2018/0028728 A1 | 2/2018 | Aarestad et al. |
| 2018/0104393 A1 | 4/2018 | Wu et al. |
| 2018/0200414 A1 | 7/2018 | Askem et al. |
| 2018/0272052 A1 | 9/2018 | Locke et al. |
| 2018/0296397 A1 | 10/2018 | Askem et al. |
| 2018/0318137 A1 | 11/2018 | Donda et al. |
| 2018/0318165 A1 | 11/2018 | Donda et al. |
| 2018/0353771 A1 | 12/2018 | Kim et al. |
| 2019/0021911 A1 | 1/2019 | Askem et al. |
| 2019/0125943 A1 | 5/2019 | Askem et al. |
| 2019/0142644 A1 | 5/2019 | Askem et al. |
| 2019/0143007 A1 | 5/2019 | Askem et al. |
| 2019/0151156 A1* | 5/2019 | Kieswetter .............. A61F 13/05 |
| 2019/0159938 A1 | 5/2019 | Askem et al. |
| 2019/0192350 A1 | 6/2019 | Gowans et al. |
| 2019/0247553 A1 | 8/2019 | Haggstrom et al. |
| 2019/0282737 A1 | 9/2019 | Beadle et al. |
| 2020/0022846 A1 | 1/2020 | Beadle et al. |
| 2021/0001022 A1 | 1/2021 | Lin |

FOREIGN PATENT DOCUMENTS

| | | |
|---|---|---|
| EP | 0512543 A2 | 11/1992 |
| EP | 1411874 A1 | 4/2004 |
| EP | 1455701 B1 | 3/2006 |
| EP | 1448261 B1 | 2/2007 |
| EP | 1476217 B1 | 3/2008 |
| EP | 1931413 A2 | 6/2008 |
| EP | 1507498 B1 | 7/2009 |
| EP | 1791579 B1 | 7/2009 |
| EP | 1947987 B1 | 5/2010 |
| EP | 1358456 B1 | 7/2010 |
| EP | 2214728 A2 | 8/2010 |
| EP | 2254537 A2 | 12/2010 |
| EP | 2340064 A1 | 7/2011 |
| EP | 2346468 A2 | 7/2011 |
| EP | 2205190 B1 | 9/2011 |
| EP | 2370116 A2 | 10/2011 |
| EP | 2531761 A1 | 12/2012 |
| EP | 2231088 B1 | 1/2013 |
| EP | 2015655 B1 | 3/2013 |
| EP | 2285323 B1 | 3/2013 |
| EP | 2049055 B1 | 4/2013 |
| EP | 2440260 B1 | 5/2013 |
| EP | 2601984 A2 | 6/2013 |
| EP | 2603699 A1 | 6/2013 |
| EP | 1893145 B1 | 7/2013 |
| EP | 2370142 B1 | 7/2013 |
| EP | 2370117 B1 | 8/2013 |
| EP | 2623137 A2 | 8/2013 |
| EP | 2263742 B1 | 9/2013 |
| EP | 2659915 A1 | 11/2013 |
| EP | 1848390 B1 | 12/2013 |
| EP | 1875081 B1 | 12/2013 |
| EP | 2271381 B1 | 12/2013 |
| EP | 2160166 B1 | 1/2014 |
| EP | 1565219 B1 | 2/2014 |
| EP | 2451498 B1 | 4/2014 |
| EP | 2051675 B1 | 6/2014 |
| EP | 1485613 B1 | 7/2014 |
| EP | 1545644 B1 | 8/2014 |
| EP | 2349154 B1 | 8/2014 |
| EP | 2146759 B1 | 9/2014 |
| EP | 2468323 B1 | 10/2014 |
| EP | 2658493 B1 | 10/2014 |
| EP | 2801388 A1 | 11/2014 |
| EP | 1850818 B1 | 12/2014 |
| EP | 2268348 B1 | 12/2014 |
| EP | 2561128 B1 | 1/2015 |
| EP | 2829287 A1 | 1/2015 |
| EP | 2683285 B1 | 2/2015 |
| EP | 2470136 B1 | 3/2015 |
| EP | 2503974 B1 | 5/2015 |
| EP | 2249894 B1 | 8/2015 |
| EP | 2802366 B1 | 8/2015 |
| EP | 2438302 B1 | 9/2015 |
| EP | 2438301 B1 | 10/2015 |
| EP | 2802304 B1 | 12/2015 |
| EP | 2852421 B1 | 1/2016 |
| EP | 2410962 B1 | 3/2016 |
| EP | 2640436 B1 | 3/2016 |
| EP | 2855937 B1 | 5/2016 |

(56) References Cited

FOREIGN PATENT DOCUMENTS

| | | | |
|---|---|---|---|
| EP | 2433594 | B1 | 6/2016 |
| EP | 2919730 | B1 | 6/2016 |
| EP | 2861869 | B1 | 7/2016 |
| EP | 2293749 | B1 | 8/2016 |
| EP | 2305327 | B1 | 10/2016 |
| EP | 2467086 | B1 | 10/2016 |
| EP | 2470135 | B1 | 10/2016 |
| EP | 2282788 | B1 | 12/2016 |
| EP | 2462956 | B2 | 3/2017 |
| EP | 3139878 | A1 | 3/2017 |
| EP | 2249761 | B1 | 4/2017 |
| EP | 1587502 | B1 | 5/2017 |
| EP | 1587554 | B1 | 5/2017 |
| EP | 2731563 | B1 | 5/2017 |
| EP | 2968871 | B1 | 7/2017 |
| EP | 2632613 | B1 | 8/2017 |
| EP | 2781208 | B1 | 8/2017 |
| EP | 2888478 | B1 | 8/2017 |
| EP | 2937107 | B1 | 8/2017 |
| EP | 3139879 | B1 | 8/2017 |
| EP | 2359784 | B1 | 9/2017 |
| EP | 3151795 | B1 | 9/2017 |
| EP | 2367518 | B1 | 10/2017 |
| EP | 3068455 | B1 | 10/2017 |
| EP | 2558046 | B2 | 11/2017 |
| EP | 2666489 | B1 | 11/2017 |
| EP | 2736548 | B1 | 11/2017 |
| EP | 3052158 | B1 | 11/2017 |
| EP | 3257486 | A1 | 12/2017 |
| EP | 2593058 | B1 | 3/2018 |
| EP | 3092988 | B1 | 3/2018 |
| EP | 3127577 | B1 | 3/2018 |
| EP | 3139880 | B1 | 3/2018 |
| EP | 2868300 | B1 | 6/2018 |
| EP | 1496822 | B1 | 8/2018 |
| EP | 2879633 | B1 | 8/2018 |
| EP | 2227203 | B1 | 9/2018 |
| EP | 3106186 | B1 | 9/2018 |
| EP | 3162330 | B1 | 9/2018 |
| EP | 3169382 | B1 | 9/2018 |
| EP | 3203953 | B1 | 9/2018 |
| EP | 2941280 | B1 | 10/2018 |
| EP | 3244852 | B1 | 10/2018 |
| EP | 2687243 | B2 | 11/2018 |
| EP | 2974754 | B1 | 11/2018 |
| EP | 3062753 | B1 | 11/2018 |
| EP | 3120879 | B1 | 12/2018 |
| EP | 3191149 | B1 | 1/2019 |
| EP | 2370130 | B1 | 3/2019 |
| EP | 3053609 | B1 | 3/2019 |
| EP | 3180048 | B1 | 3/2019 |
| EP | 3143974 | B1 | 4/2019 |
| EP | 3487547 | A1 | 5/2019 |
| EP | 2285432 | B2 | 6/2019 |
| EP | 3187209 | B1 | 6/2019 |
| EP | 2740501 | B1 | 7/2019 |
| EP | 3050545 | B1 | 7/2019 |
| EP | 3311856 | B1 | 7/2019 |
| EP | 3319656 | B1 | 8/2019 |
| EP | 2355762 | B1 | 9/2019 |
| EP | 2822613 | B1 | 9/2019 |
| EP | 2863855 | B1 | 9/2019 |
| EP | 2482912 | B1 | 10/2019 |
| EP | 3038667 | B1 | 10/2019 |
| EP | 3129095 | B1 | 10/2019 |
| EP | 3191150 | B1 | 10/2019 |
| EP | 3280466 | B1 | 10/2019 |
| EP | 3287113 | B1 | 10/2019 |
| EP | 3281650 | B1 | 11/2019 |
| EP | 2244756 | B1 | 12/2019 |
| EP | 2968702 | B1 | 12/2019 |
| FR | 2939320 | A1 | 6/2010 |
| GB | 2511523 | A | 9/2014 |
| JP | H04354722 | A | 12/1992 |
| JP | 2016043178 | A | 4/2016 |
| RU | 131622 | U1 | 8/2013 |
| WO | WO-2009098696 | A2 | 8/2009 |
| WO | WO-2009120951 | A2 | 10/2009 |
| WO | WO-2011135285 | A1 | 11/2011 |
| WO | WO-2011144888 | A1 | 11/2011 |
| WO | WO 2012/057881 | | 5/2012 |
| WO | WO-2014099709 | A1 | 6/2014 |
| WO | WO 2016/061146 | | 4/2016 |
| WO | WO 2016/107775 | | 7/2016 |
| WO | WO-2016126560 | A1 | 8/2016 |
| WO | WO-2017079174 | A1 | 5/2017 |
| WO | WO-2017196888 | A1 | 11/2017 |
| WO | WO-2018056060 | A1 | 3/2018 |
| WO | WO-2018115461 | A1 | 6/2018 |
| WO | WO-2018156730 | A1 | 8/2018 |
| WO | WO-2018158250 | A1 | 9/2018 |
| WO | WO-2018162613 | A1 | 9/2018 |
| WO | WO-2018164803 | A1 | 9/2018 |
| WO | WO-2018185138 | A1 | 10/2018 |
| WO | WO-2018192978 | A1 | 10/2018 |
| WO | WO-2018206420 | A1 | 11/2018 |
| WO | WO-2019053101 | A1 | 3/2019 |
| WO | WO-2019086332 | A1 | 5/2019 |
| WO | WO-2019086341 | A1 | 5/2019 |
| WO | WO-2019086475 | A1 | 5/2019 |

OTHER PUBLICATIONS

International Search Report and Written Opinion, re PCT Application No. PCT/EP2017/081959, mailed May 9, 2018.
International Preliminary Report on Patentability for Application No. PCT/EP2017/081959, mailed on Jun. 27, 2019, 14 pages.

* cited by examiner

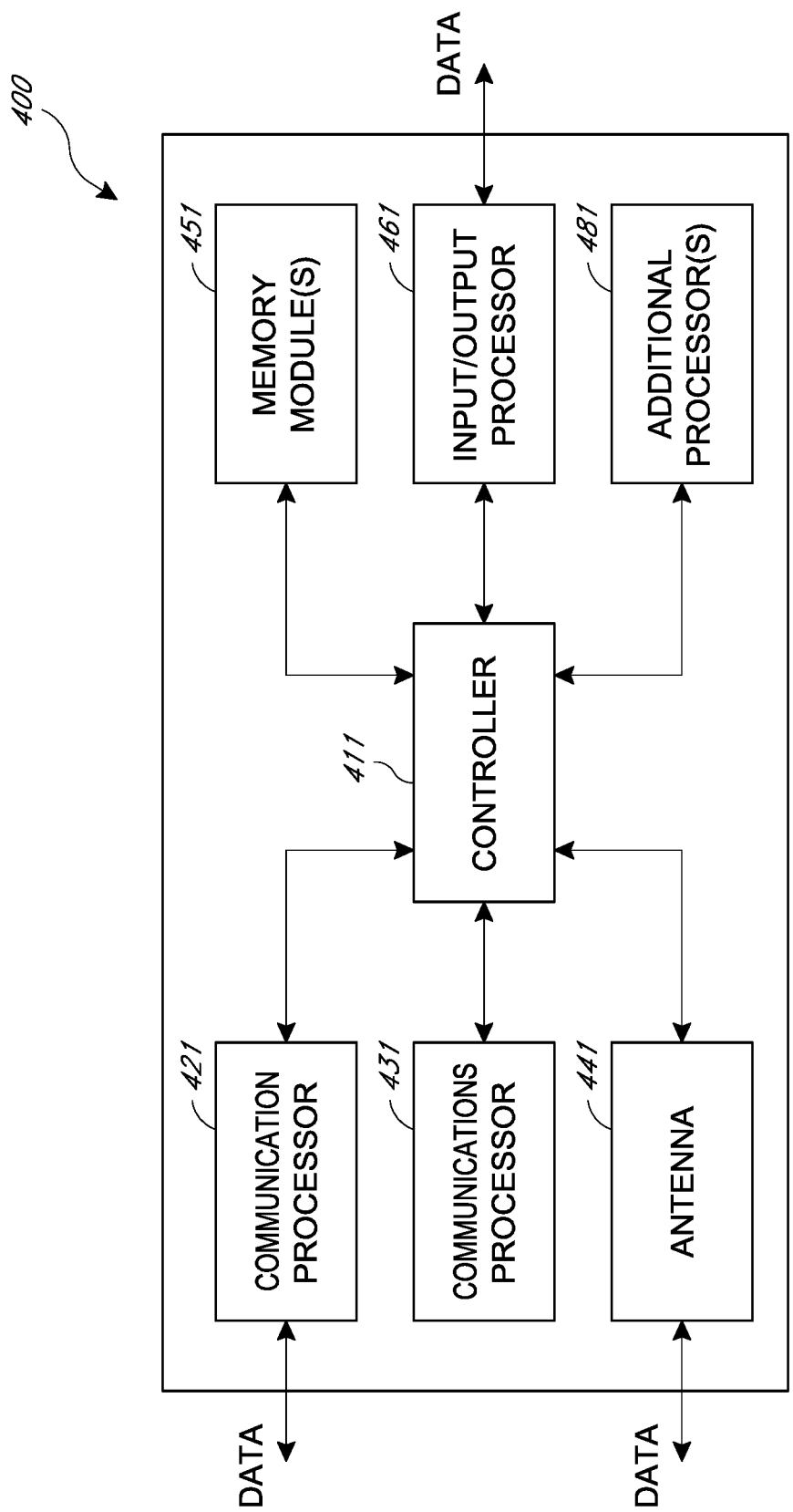

PRESSURE WOUND THERAPY STATUS INDICATION VIA EXTERNAL DEVICE

CROSS-REFERENCE TO RELATED APPLICATIONS

The present application is a U.S. national stage application of International Patent Application No. PCT/EP2017/081959, filed Dec. 8, 2017, which claims priority to benefit to U.S. Provisional Application Nos. 62/464,173, entitled "PRESSURE WOUND THERAPY STATUS INDICATION VIA EXTERNAL DEVICE," filed Feb. 27, 2017 and 62/433,179, entitled "PRESSURE WOUND THERAPY STATUS INDICATION VIA EXTERNAL DEVICE," filed Dec. 12, 2016, each of which is hereby incorporated herein by reference in its entirety.

BACKGROUND

Embodiments described herein relate to apparatuses, systems, and methods the treatment of wounds, for example using dressings in combination with negative pressure wound therapy.

Negative pressure wound therapy, which involves the controlled application of sub-atmospheric pressure to a wound environment, is widely recognized as a beneficial mechanism for improving the healing rate of a wound. Sometimes referred to as vacuum assisted closure, topical negative pressure therapy, or reduced pressure wound therapy, negative pressure wound therapy assists in the closure and healing of wounds by reducing tissue oedema; encouraging blood flow; stimulating the formation of granulation tissue; removing excess exudates, and may reduce bacterial load and thus reduce the potential for infection of the wound. Furthermore, negative pressure wound therapy permits less outside disturbance of the wound and promotes more rapid healing.

SUMMARY

In some embodiments, a negative pressure wound therapy system includes a negative pressure therapy apparatus configured to apply negative pressure to a wound of a patient. The negative pressure therapy apparatus can include a wound dressing configured to be placed over the wound, a negative pressure source supported by the wound dressing, and a controller that includes one or more processors. The controller can be configured to determine one or more operating data of the negative pressure therapy apparatus, and transmit the one or more operating data. The negative pressure wound therapy system can further include a wireless communication device. The wireless communication device can include a controller having one or more processors. The controller of the wireless communication device can be configured to be communicatively coupled to the negative pressure therapy apparatus and can be further configured to receive the one or more operating data transmitted by the controller of the negative pressure therapy apparatus and output the received one or more operating data.

The system of the preceding paragraph may also include any combination of the following features described in this paragraph, among others described herein. The controller of the negative pressure therapy apparatus can be configured to transmit the one or more operating data responsive to at least one of an occurrence of an event, an expiration of a time interval, or a request received from the wireless communication device. The one or more operating data can include one or more of power status data, error data, negative pressure data, wound data, dressing data, connection data, activity data, or patient data.

The system of any of the preceding paragraphs may also include any combination of the following features described in this paragraph, among others described herein. The wound can be located in an area that is outside of the patient's vision or reach. The area can include at least one of a back, shoulder, leg, hip, foot, or buttocks of the patient. The area can include at least a portion of the patient's posterior.

The system of any of the preceding paragraphs may also include any combination of the following features described in this paragraph, among others described herein. The system can include another negative pressure therapy apparatus. The another negative pressure therapy apparatus can include another wound dressing configured to be placed over another wound and another negative pressure source supported by the another wound dressing. The controller of the wireless communication device can be further configured to be communicatively coupled to the another negative pressure therapy apparatus. The controller of the wireless communication device can be further configured to receive another one or more operating data transmitted by another controller of the another negative pressure therapy apparatus; and output the received one or more operating data and the received another received one or more operating data.

The system of any of the preceding paragraphs may also include any combination of the following features described in this paragraph, among others described herein. The system can include another wireless communication device. The another wireless communication device can include a controller with one or more processors. The another wireless communication device can be configured to be communicatively coupled to the negative pressure therapy apparatus. The wireless communication device can further include a display configured to output the one or more operating data. The wireless communication device can include a housing enclosing a memory and the controller of the wireless communication device, the housing sized to be worn by the patient or by a caregiver. The wireless communication device can be worn on a wrist of a patient or a caregiver. For example, the wireless communication device can be a watch, wristband, or the like.

In some embodiments, a wireless communication device for communicating with a negative pressure therapy apparatus can include a memory and a controller including one or more processors. The controller can be configured to generate a request for one or more operating data of a negative pressure therapy apparatus. The negative pressure therapy apparatus can include a wound dressing configured to be placed over a wound of a patient and a negative pressure source supported by the wound dressing. The negative pressure apparatus can be configured to provide negative pressure therapy to the wound. The request can be based upon at least one of an occurrence of an event, a received user input, or an expiration of a time interval. The controller can be further configured to transmit the request to the negative pressure therapy apparatus, receive the one or more operating data from the negative pressure therapy apparatus, and output the one or more operating data.

The device of the preceding paragraph may also include any combination of the following features described in this paragraph, among others described herein. The one or more operating data can include one or more of power status data, error data, negative pressure data, wound data, dressing data, connection data, activity data, or patient data. The wound can be located in an area that is outside of the patient's vision or reach. The area can include at least one of a back, shoulder, leg, hip, foot, or buttocks of the patient. The area can include at least a portion of the patient's posterior. The device can further include a display configured to output the one or more operating data.

The device of any of the preceding paragraphs may also include any combination of the following features described in this paragraph, among others described herein. The device can include a housing enclosing the memory and the controller. The housing can be sized to be worn by the patient or by a caregiver. The housing can be sized to be worn on a wrist. The controller can be further configured to generate another request for one or more operating data of another negative pressure therapy apparatus comprising another wound dressing configured to be placed over another wound and another negative pressure source supported by the another wound dressing. The controller can be further configured to transmit the another request. The controller can be further configured to receive the one or more operating data of the another negative pressure therapy apparatus. The controller can be further configured to output the one or more operating data of the negative pressure therapy apparatus and the one or more operating data of the another negative pressure therapy apparatus.

In some embodiments, a non-transitory computer storage medium can include instructions for wirelessly communicating with a plurality of negative pressure therapy apparatuses. The instructions when executed by a processor can cause the processor to perform a method that includes generating a request for one or more operating data of a negative pressure therapy apparatus. The negative pressure therapy apparatus can be configured to be placed over a wound of a patient and further configured to provide negative pressure therapy to the wound. The request can be based upon at least one of an occurrence of an event, a received user input, or an expiration of a time interval. The method can further include transmitting the request to the negative pressure therapy apparatus, receiving the one or more operating data from the negative pressure therapy apparatus, and outputting the one or more operating data.

The non-transitory computer storage medium of the preceding paragraph may also include any combination of the following features described in this paragraph, among others described herein. Outputting the one or more operating data can include displaying the one or more operating data. The wound can be located in an area that is outside of the patient's vision or reach. The area can include at least one of a back, shoulder, leg, hip, foot, or buttocks of the patient. The area can include at least a portion of the patient's posterior. The one or more operating data can include one or more of power status data, error data, negative pressure data, wound data, dressing data, connection data, activity data, or patient data.

The non-transitory computer storage medium of any of the preceding paragraphs may also include any combination of the following features described in a paragraph, among others described herein. The method can further include generating another request for another one or more operating data of another negative pressure therapy apparatus configured to be placed over another wound of the patient and further configured to provide negative pressure therapy to the another wound. The method can further include transmitting the another request to the another negative pressure therapy apparatus. The method can further include receiving the another one or more operating data from the another negative pressure therapy apparatus. The method can further include outputting the one or more operating data and the another one or more operating data. The another one or more operating data can include one or more of: power status data, error data, negative pressure data, wound data, dressing data, connection data, activity data, or patient data.

In some embodiments, a wireless communication device for communicating with a negative pressure wound therapy system can can include a memory and a controller including one or more processors. The controller can be configured to wirelessly communicate with a plurality of negative pressure apparatuses. The plurality of negative pressure apparatuses can be configured to be positioned on a patient and further configured to provide negative pressure therapy to a plurality of wounds. Each of the plurality of negative pressure apparatuses can include a wound dressing that can be configured to be placed over a wound of the patient. Each of the plurality of negative pressure apparatuses can further include a negative pressure source supported by the wound dressing, and a controller that can be configured to control the negative pressure source. The controller can be further configured to receive first and second operating data associated with provision of negative pressure therapy by at least first and second negative pressure apparatuses, respectively, and generate a notification based on the received operating data. The notification can include information identifying the first and second negative pressure apparatuses and the respective first and second operating data.

The device of the preceding paragraph may also include any combination of the following features described in this paragraph, among others described herein. The first and second operating data can include one or more of power status data, error data, negative pressure data, wound data, dressing data, connection data, activity data, or patient data.

In some embodiments, a method of communicating within a negative pressure wound therapy system can include wirelessly communicating, using a wireless communication device positioned on a patient's wrist, with a negative pressure apparatus. The negative pressure apparatus can include a wound dressing positioned over a wound of a patient and a negative pressure source supported by the wound dressing. The negative pressure therapy device can provide negative pressure therapy to the wound. The wireless communication can be based upon at least one of an occurrence of an event, a received user input, or an expiration of a time interval. The method can further include outputting one or more operating data associated with provision of negative pressure therapy by the negative pressure apparatus.

The method of the preceding paragraph may also include any combination of the following features described in this paragraph, among others described herein. Wirelessly communication can include receiving, at the wireless communication device, the one or more operating data from the negative pressure therapy apparatus. Wirelessly communicating can further include generating, at the wireless communication device, a request for the one or more operating data of the negative pressure therapy apparatus. The request can be based upon the at least one of an occurrence of an event, a received user input, or an expiration of a time interval. Wirelessly communicating can further include transmitting the request to the negative pressure therapy apparatus. The method can further include generating another request for one or more operating data of another negative pressure therapy apparatus. The another negative pressure therapy apparatus can include another wound dressing positioned over another wound of the patient and another negative pressure source supported by the another wound dressing. The another negative pressure therapy device can provide negative pressure therapy to the another wound. The method can further include transmitting the another request, receiving the one or more operating data of the another negative pressure therapy apparatus, and outputting the one or more operating data of the another negative pressure therapy apparatus. The wound can be located in an area that is outside of the patient's vision or reach. The area can include at least one of a back, shoulder, leg, hip, foot, or buttocks of the patient. The area can include at least a portion of the patient's posterior.

Any of the features, components, or details of any of the arrangements or embodiments disclosed in this application, including without limitation any of the pump embodiments and any of the negative pressure wound therapy embodiments disclosed below, are interchangeably combinable with any other features, components, or details of any of the arrangements or embodiments disclosed herein to form new arrangements and embodiments.

BRIEF DESCRIPTION OF THE DRAWINGS

FIG. 4 illustrates an electrical component schematic of a wireless communication device (WCD) according to some examples.

DETAILED DESCRIPTION

Figure 1A:
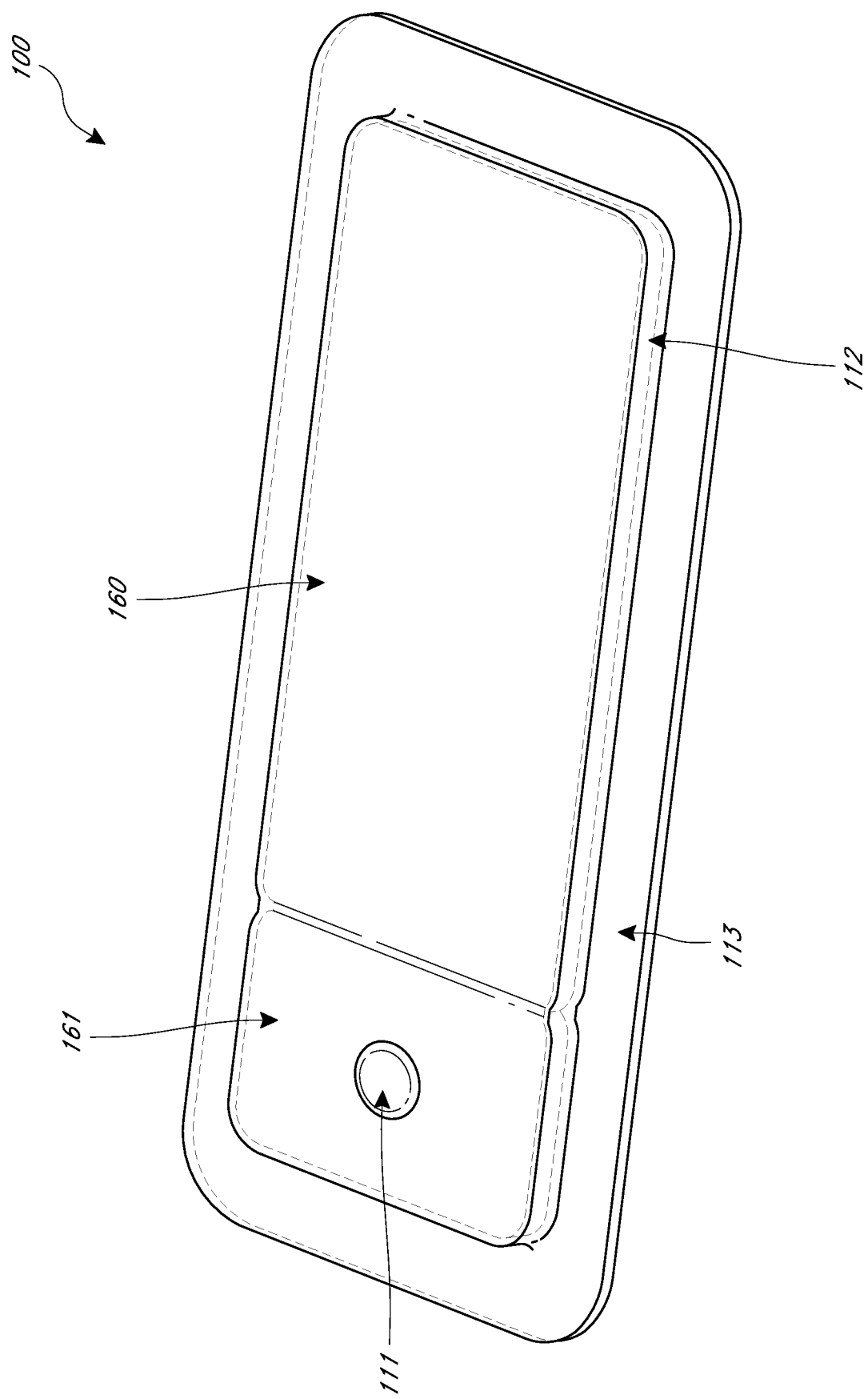
FIG. 1A illustrates a perspective view of a negative pressure therapy apparatus according to some embodiments.

Embodiments disclosed herein relate to apparatuses and methods of negative pressure therapy include a wireless communication device configured to be communicatively coupled to a negative pressure therapy apparatus.

It will be understood that embodiments of the present disclosure are generally applicable to use in topical negative pressure (TNP) therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as −X mmHg, represent pressure levels relative to ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below, for example, 760 mmHg or, in other words, an absolute pressure of (760-X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg). In some embodiments, local ambient atmospheric pressure is used as a reference point, and such local atmospheric pressure may not necessarily be, for example, 760 mmHg.

The negative pressure range for some embodiments of the present disclosure can be approximately −80 mmHg, or between about −20 mmHg and −200 mmHg. Note that these pressures are relative to ambient atmospheric pressure, which can be 760 mmHg. Thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus.

In some embodiments, negative pressure wound therapy systems can have a variety of components including a source of negative pressure (such as a pump), other electrical components, and a wound dressing. While some negative pressure wound therapy systems include a negative pressure source located in a remote location from the wound dressing, it can be desirable (for example, to provide increased system portability) for the negative pressure source and other electronic components to be incorporated into the wound dressing. In such instances, user interface component(s) (such as button(s), switch(es), speaker(s), screen(s), etc.) and the like are also combined with the wound dressing. However, when user interface components of the negative pressure wound therapy system are incorporated into the wound dressing, if the user's wound, and thus the placement of the wound dressing, is outside a patient's vision or reach (for instance, on the user's back, posterior, shoulder, leg, hip, foot, or buttocks), the user's ability to interface with the negative pressure wound therapy system can be limited. In some embodiments, a wireless communication device, external to the integrated negative pressure therapy apparatus, can allow the user or another individual (such as a caregiver) to communicate with the negative pressure wound therapy system. While certain embodiments described herein are directed to or utilize a wireless communication device (WCD), the communication device of any of the described embodiments can support wired communication.

Some embodiments are directed to a system, computer-readable medium, method, and apparatus for communicating with a negative pressure therapy apparatus that includes a wound dressing and a negative pressure source supported by the wound dressing. According to certain aspects, a negative pressure wound therapy system can include a negative pressure therapy apparatus configured to apply negative pressure to a wound of a patient. The negative pressure therapy device can include a wound dressing configured to be placed over the wound, a negative pressure source supported by the wound dressing, and a controller. The controller can include a processor configured to determine operating data of the negative pressure therapy apparatus, and transmit the operating data. The negative pressure wound therapy system can further include a wireless communication device communicatively coupled to the negative pressure therapy apparatus and configured to receive and output the operating data.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sternotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Figure 1B:
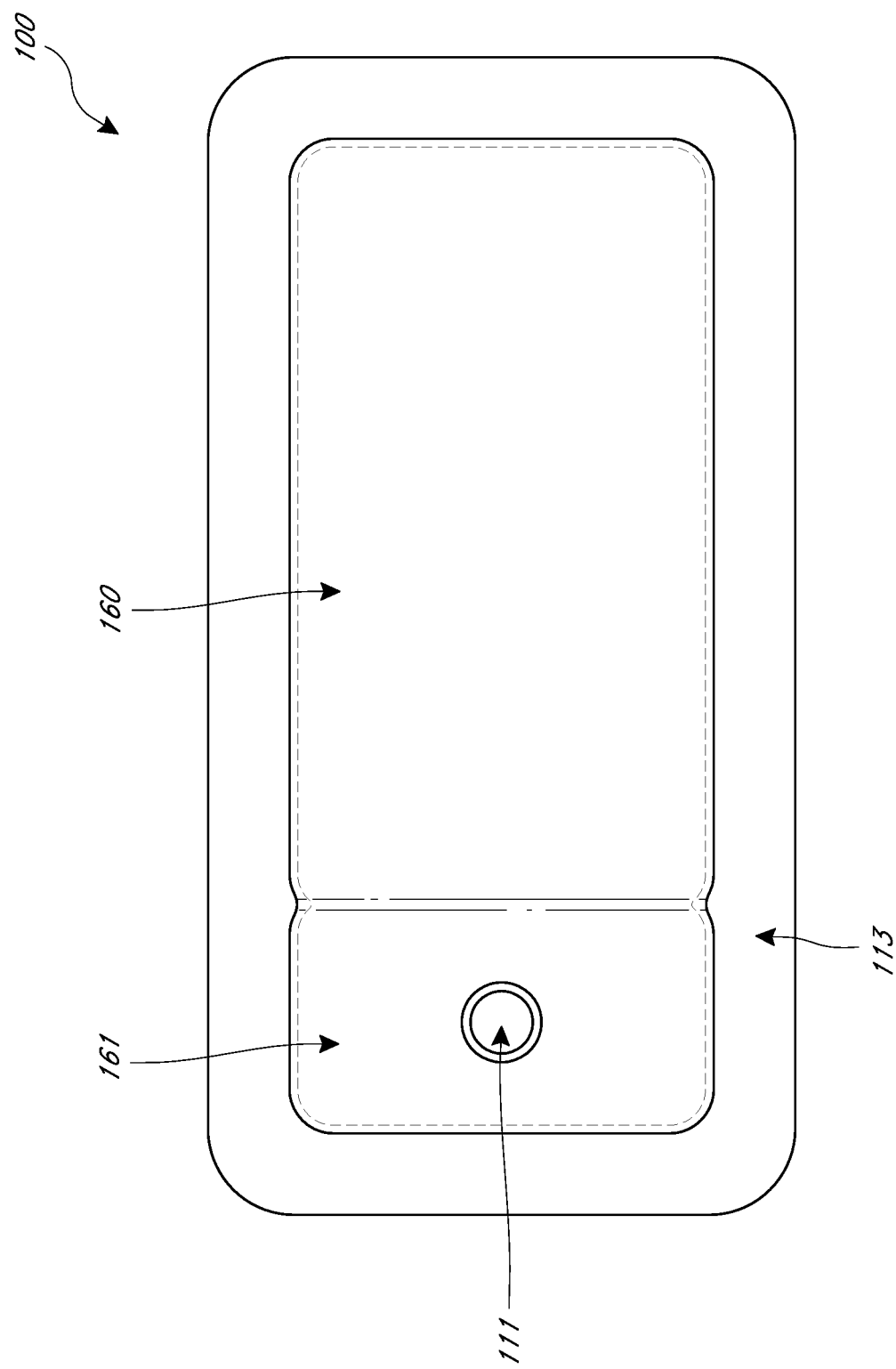
FIG. 1B illustrates a top view of the negative pressure therapy apparatus of FIG. 1A.

FIGS. 1A-1B illustrates a wound dressing 100 incorporating the source of negative pressure and/or other electronic components within the wound dressing. As is illustrated, the negative pressure therapy apparatus 100 incorporates a negative pressure source (such as the pump) and/or other electronic components within a wound dressing. The apparatus 100 is illustrated as a wound dressing configured to be placed over a wound. The wound dressing can include an electronics area 161 and an absorbent area 160. The dressing can comprise a wound contact layer (not shown) and a moisture vapor permeable film or cover layer 113 positioned above the contact layer and other layers of the dressing. The wound dressing layers and components of the electronics area as well as the absorbent area can be covered by one continuous cover layer 113 as shown in FIGS. 1A-1B.

The area 161 can include an electronics cassette and/or electronics unit positioned below a cover layer 113 of the dressing. The negative pressure source can be positioned in the area 161. In some embodiments, the electronics unit can be surrounded by a material to enclose or encapsulate the negative pressure source and electronics components. The electronics unit can be in contact with the dressing layers in the area 160 and be covered by the cover layer 113. The electronics unit includes a lower or wound facing surface that is closest to the wound (not shown) and an opposite, upper surface, furthest from the wound when the wound dressing is placed over a wound.

The electronics area 161 can include a source of negative pressure (such as a pump) and some or all other components of the TNP system, such as power source(s), sensor(s), connector(s), user interface component(s) (such as button(s), switch(es), speaker(s), screen(s), etc.) and the like, that can be integral with the wound dressing. For example, the electronics area 161 can include a button or switch 111 as shown in FIG. 1A-1B. The button or switch 111 can be used for operating the pump (e.g., turning the pump on/off).

The absorbent area 160 can include an absorbent material 112 and can be positioned over the wound site. The electronics area 161 can be positioned away from the wound site, such as by being located off to the side from the absorbent area 160. The electronics area 161 can be positioned adjacent to and in fluid communication with the absorbent area 160 as shown in FIGS. 1A-1B. In some embodiments, each of the electronics area 161 and absorbent area 160 may be rectangular in shape and positioned adjacent to one another.

In some embodiments, additional layers of dressing material can be included in the electronics area 161, the absorbent area 160, or both areas. In some embodiments, the dressing can comprise one or more spacer layers and/or one or more absorbent layer positioned above the contact layer and below the wound cover layer 113 of the dressing.

In operation, the wound dressing is placed over a wound such as to provide a substantially fluid-tight seal over the wound. For example, the cover layer can extend beyond the combined areas 161 and 160 and can include adhesive that seals the dressing to skin surrounding the wound. As another example, the bottom of the dressing can have adhesive. The negative pressure source provides negative pressure to the wound and, as a result, fluid (such as exudate) is aspirated from the wound. The removed fluid can be trapped or otherwise stored in the absorbent. Although illustrated without a canister, the negative pressure apparatus 100 can operate with a canister configured to store at least some fluid removed from the wound.

The negative pressure source and/or the electronics can be supported by the wound dressing, such as embedded in the dressing as is shown in FIGS. 1A-1B. In other embodiments, one or more of the negative pressure source and/or the electronics can be partially embedded in the wound dressing, positioned on the top, bottom, or side of the wound dressing, and the like. Additional embodiments of negative pressure apparatuses are described in Appendices A and B, each of which is incorporated by reference in its entirety.

In some examples, the negative pressure apparatus 100 can determine and/or record one or more operating data. Operating data can take many forms including patient data and negative pressure apparatus 100 data. For instance, operating data can include power status data, error data, negative pressure data, dressing data, connection data, activity data, patient data, and the like. It should be noted that such operating data categories can overlap.

Power status data can include any data relating to operating conditions or power status of the negative pressure apparatus 100. For instance, power status data can include data reflecting battery status, power consumption, power level, operating conditions (normal, error, etc.), system power status (such as on/off, standby, pause, etc.), and the like.

Error data can include any data relating to negative pressure apparatus 100 malfunctions or any abnormality in the operation of the negative pressure therapy apparatus. For instance, error data can include data reflecting a dressing problem, pressure leak, under-pressure, over-pressure, pairing/connection problem, compliance monitoring, etc.

Negative pressure data can include any data relating to operation of the negative pressure source. For instance, negative pressure data can include data reflecting pressure levels, negative pressure source activity data, loss of suction, over-pressure, under-pressure and the like.

Dressing data can include dressing capacity, saturation level of the dressing, orientation/motion data, suction data, etc. Connection data can include information such as pairing status of a communication device, connection status, etc.

Operating data can include activity data (such as log(s)), which includes therapy delivery information, such as therapy duration; alarm log(s), which includes alarm type and time of occurrence; error log(s), which includes internal error information, transmission errors, and the like; therapy duration information, which can be computed hourly, daily, and the like; total therapy time, which includes therapy duration from first applying a particular therapy program or programs; lifetime therapy information; device information, such as the serial number, software version, battery level, etc.; location tracking/device location information; patient information; and so on.

Patient data can include any data relating to physiological data or patient wound data. For instance, patient data can include physiological data such as blood pressure, heart rate, patient activity (such as indication that the patient has turned, moved, etc.) and the like. It can also include data reflecting wound data such as wound healing status, estimation of healing time, percent healed, etc.

Wound healing status data can be determined by the wound apparatus device in a variety of ways. For instance, the negative pressure therapy apparatus can be configured to monitor blood flow of the wound area and collect and record such blood flow data. The rate of blood flow at the wound site can be used to determine a stage in the healing process of the wound (for example, low blood flow can indicate an early stage of healing while higher blood flow can indicate the wound is close to being healed). The blood flow data can be processed by the negative pressure therapy apparatus, the WCD, or a remote device and used to determine what stage the wound is of the healing process. As such, the WCD, negative pressure therapy apparatus, or remote device can be configured to communicate that the wound is not healed, partially healed, completely healed, or the wound is healed within a percentage range (such as 40-50%, 50-60%, 70-80%, 80-90%, or the like). As another example, the negative pressure therapy apparatus can monitor the rate of fluid removal from the wound and determine the stage of the healing process. In some circumstances, reduction in the rate of fluid removal can indicate that the wound is healing.

Figure 2:
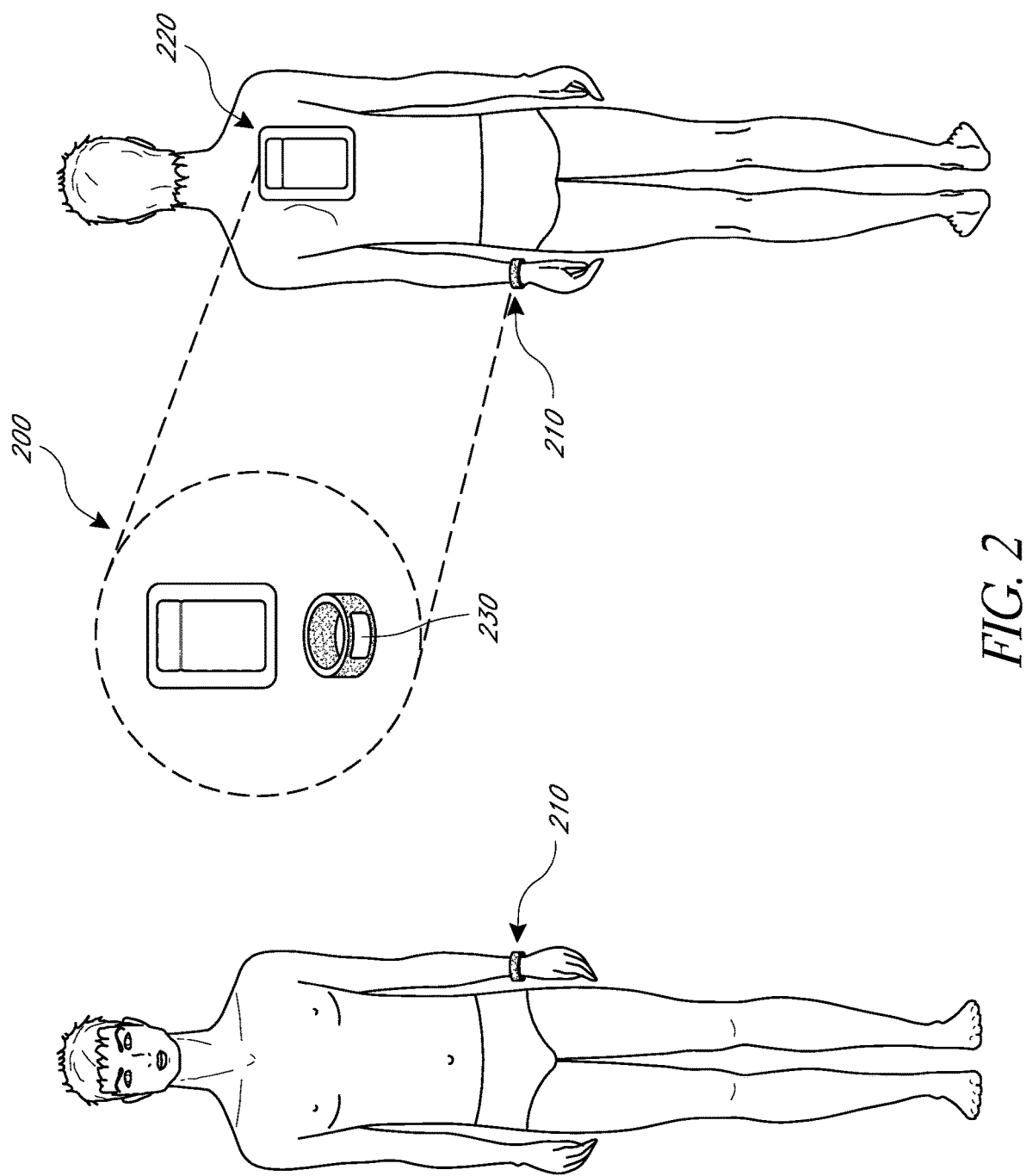
FIG. 2 illustrates a negative pressure wound therapy system according to some embodiments.

FIG. 2 illustrates a negative pressure wound therapy system 200 comprising a WCD 210 configured to communicate with a negative pressure therapy apparatus 220 according to some embodiments. Although FIG. 2 depicts the WCD 210 having a housing sized as a wearable wristband, the WCD 210 can take many forms including wearable and non-wearable devices. For instance, the WCD 110 can take the form of a mobile phone, tablet, computer, MP3 player, pager, watch, PDA, necklace, ring, arm band, belt, chest strap or any device that can be configured to trigger indications or alerts to a user or another individual. Additionally, the WCD can take the form of an application or program, for instance a smart phone application.

The negative pressure wound therapy system 200 can include the negative pressure therapy apparatus 220 configured to apply negative pressure to a wound of a patient and the WCD 210 configured to be communicatively coupled to the negative pressure therapy apparatus 220. The negative pressure therapy apparatus 220 can be the same as the negative pressure therapy apparatus 100 of FIGS. 1A-1B. As is illustrated, the negative pressure therapy apparatus 220 is positioned on the patient's back, which makes it difficult to operate the apparatus 220. In other circumstances, the negative pressure therapy apparatus 220 can be positioned on another place on the body that is difficult to access. For example, the wound (or negative pressure therapy apparatus 220) can be located in an area that is outside of the patient's vision or reach (such as on at least a portion of the patient's posterior, back, shoulder, leg, hip, foot, or buttocks). To solve the problems of operating the negative pressure therapy apparatus 220, the negative pressure therapy apparatus 220 and the WCD 210 can be configured to wirelessly communicate with each other over wireless networks (such as Wi-Fi internet networks, Bluetooth networks, etc.), telecommunications networks (such as 3G networks, 4G networks, etc.) or any other wireless or wired communication method.

In some cases, the negative pressure therapy apparatus 220 can communicate operating data (e.g., operating data can include power status data, error data, negative pressure data, dressing data, connection data, activity data, patient data, dressing data, or the like) to the WCD 210. For example, the negative pressure therapy apparatus 220 can transmit operating data (a) upon the occurrence of an event (such as a detected operating condition and/or an error) (b) in repeated time intervals, (such as, once every minute, ten minutes, thirty minutes, 2 hours, 4 hours, etc.) and/or (c) in response to a received request. One or more triggers and/or parameters for transmitting the operating data can be configured by a user, such as the patient, caregiver, etc. An "event" can, for example, be any deviation in measured, tracked, or calculated operating data, such as a detected error, a change in power status, an alarm indicator, an event defined by a user, or the like.

The negative pressure therapy apparatus 220 can be interrogated by the WCD 210. For example, the negative pressure therapy apparatus 220 can be responsive to interrogation by communicating operating data. Communication can be done over secure communications protocols. By way of example, the negative pressure therapy apparatus 220 can release internal data only to the WCD 210 with the correct passwords and/or data protocols. As another example, the negative pressure therapy apparatus 220 and the WCD 210 are securely paired prior to communication of data. Although the illustrated example of FIG. 2 depicts a single WCD 210, it will be understood that the negative pressure wound therapy system 200 can include more than one WCD 210 configured to communicate with a negative pressure therapy apparatus 220. For example, a first WCD 210 can transmit a request for reception by a negative pressure therapy apparatus 220. In response to receiving the request by the first WCD, the negative pressure therapy apparatus 220 can broadcast operating data capable of being received by at least the first WCD and a second WCD. In examples such as these, the first WCD can be used by a first user, such as a patient, and the second WCD can be used by a second user, such as a caregiver, or vice versa. As another example, the caregiver can use the first WCD to transmit one or more commands to operate the negative pressure therapy apparatus 220, while patient can use the second WCD to only receive operating data. As such, the WCD can operate in several different modes, including a caregiver mode and a patient mode.

For instance, it is desirable for a caregiver to know whether a patient's negative pressure therapy apparatus 220 is functioning properly. As a result, the caregiver can use a first WCD to transmit a request to the patient's negative pressure therapy apparatus. In response to receiving the request from the first WCD, the patient's negative pressure therapy apparatus can transmit operating data to just one or both the first WCD operated by the caregiver and a second WCD, for instance, operated by the patient.

A negative pressure therapy apparatus 220 can simultaneously receive and/or respond to requests from one or more WCDs. In some aspects, the one or more WCDs can communicate with a negative pressure therapy apparatus 220 using handover communications. For instance, the negative pressure therapy apparatus can determine which WCD among a plurality of WCDs is closest and/or would have the most reliable communication connection with the negative pressure therapy apparatus. Likewise, each of the WCDs of a plurality of WCDs could make this determination. For example, upon determining that a second WCD is a more suitable connection (such as based on proximity, reliability, etc.), a first WCD in communication with the negative pressure therapy apparatus can handover communication to a second WCD.

Although the illustrated example of FIG. 2 depicts a single negative pressure therapy apparatus 220, in some aspects, the negative pressure wound therapy system 200 can include two or more negative pressure therapy apparatuses, which can be positioned to treat various different wounds of a patient and/or wounds of different patients. For example, a communication link can be established between a first WCD and a first negative pressure therapy apparatus and the first WCD and a second negative pressure therapy apparatus.

For example, it can be desirable for a caregiver to monitor more than one patient, each patient using a negative pressure therapy apparatus. The WCD 210 can communicate (e.g. paired via Bluetooth, connected via Wi-Fi, etc.) with a first negative pressure therapy apparatus treating a wound of patient one and a second negative pressure therapy apparatus treating a wound of patient two. In these examples, WCD can be configured to communicate with the first and second negative pressure therapy apparatuses individually or as a group. Using a user interface of the WCD, a nurse can choose to request operating data from one or both connected negative pressure therapy apparatuses. In response to the request, each negative pressure therapy apparatus can transmit at least the requested operating data to the WCD. The WCD can receive, store and process the transmitted data and generate an output based at least upon the received data.

In examples such as these, it can be desired for the two or more negative pressure therapy apparatuses to include a patient or apparatus identifier along with its response or otherwise associate transmitted data with identification of a transmitting apparatus. For instance, the patient or apparatus identifier can be received by the WCD and used to generate a log of patient or apparatus specific data. In other instances, the identifier can be used by the WCD to identify which information to display. In cases when more than one WCD communicates data with a negative pressure apparatus, identifying information of a WCD can similarly be transmitted to the negative pressure therapy apparatus.

In some cases, multiple negative pressure therapy apparatuses can communicate with multiple WCDs.

A WCD 210 can be configured to transmit one or more commands or instructions to a negative pressure therapy apparatus 220. These instructions can be created by a user of the WCD 210 or can be automatically created by the WCD 210. The instructions sent by the WCD 210 can alter operating settings (thereby controlling operating data) or any other negative pressure apparatus setting. For instance, the WCD 210 can instruct the negative pressure therapy apparatus 220 to pause, turn on, turn off, increase pressure, reduce pressure, etc. As another example, the WCD 210 can transmit a command to active the negative pressure source to apply negative pressure to the wound, a command to change the negative pressure level, a command to deactivate the negative pressure source, and the like.

The WCD 210 can be pre-programmed to work with the negative pressure therapy apparatus 220. For instance, the WCD 210 can be pre-programmed to communicate exclusively with a specific negative pressure apparatus. As another example, the WCD 210 can be pre-programmed to communicate with a negative pressure apparatus 220, but not exclusively, and the WCD 210 can accept other connections. In some examples, the WCD 210 is not pre-programmed to communicate with any specific negative pressure device but can be configured to communicate with a negative pressure device. Similarly, a negative pressure apparatus 220 can be pre-programmed to communicate with a WCD or may not be programmed but can be configured to communicate with a WCD 210.

Although not shown, in some examples, the negative pressure therapy apparatus 220 and/or WCD 210 can communicate with a remote computer or server, for instance, via the cloud. The remote computer or server can include a data storage processor and a web interface for accessing the remote computer. In some instances, the remote computer or server can function as a communication device 210.

The WCD 210 can provide indicators, signals and/or alarms to communicate data to the user. For instance, the WCD 210 can include one or more speaker(s), display(s), light source(s), tactile devices, etc., and/or combinations thereof. The indicators can include any visual, audible, and tactile indications. For instance, if the user is blind, the WCD 210 can be configured to provide an audible alarm and/or vibration. If the user is deaf, the WCD 210 can be configured to provide a visual alarm and/or vibration. In some examples, the user can change the type of indication based on his or her preference.

A WCD can comprise a display, for example display 230 as illustrated in FIG. 2. The display 230 can be a touch screen display or other screen, such as an LCD screen. In some examples, the display can provide a user with an option to select one or more operating data to view. For instance, the display can provide a list of operating data options for selection by a user. In response to user selection of an operating data option, the WCD can communicate with a negative pressure therapy apparatus and generate an output on the display corresponding to the operating data option selected by the user. In other examples, the WCD can provide at least one real time operating data from the negative pressure therapy apparatus to the display.

The display 230 can include one or more indicators. For instance, an active (such as lit) indicator of the one or more indicators can represent a one or more operating data of the negative pressure therapy apparatus. For example, a dressing indicator of the one or more indicators can provide an indication as to presence of leaks in the negative pressure therapy apparatus, and an active dressing indicator can represent a leak. As another example, a dressing capacity indicator of the one or more indicators can provide an indication as to the remaining fluid capacity of the wound dressing or canister, and an active dressing capacity indicator can represent that the wound dressing or canister is at or nearing capacity. As yet another example, a battery indicator of the one or more indicators can provide an indication as to remaining capacity or life of a power source, such as batteries, and an active battery indicator can represent a low capacity. In some embodiments, the one or more indicators can represent a combination of one or more of the above events of the negative pressure therapy apparatus or other operating or failure conditions of the negative pressure therapy apparatus.

The WCD 210 can be powered in a number of ways including but not limited to battery power, harvesting a user's body heat to convert into electricity, wireless power transfer, and the like. A battery can be any suitable battery for use in the WCD, including, for example, a lithium-ion battery, lithium polymer battery, or the like, and can be rechargeable. The battery can be charged in any suitable way including but not limited to inductive charging.

In some cases, the WCD 210 can harvest a user's body heat and convert it into electricity sufficient to power some or all of the WCD 210. In some examples, the WCD 210 includes a heat sink which converts body heat into electrical power. However, in some cases, heat sinks can make the WCD 210 heavy, stiff, and/or bulky. Thus, in other examples, the WCD 210 can make use of thermoelectric generators (TEGs) to generate electricity by making use of the temperature difference between the user's body and the ambient air. In some embodiments, the negative pressure therapy apparatus can be powered using one or more technologies described herein.

Figure 3:
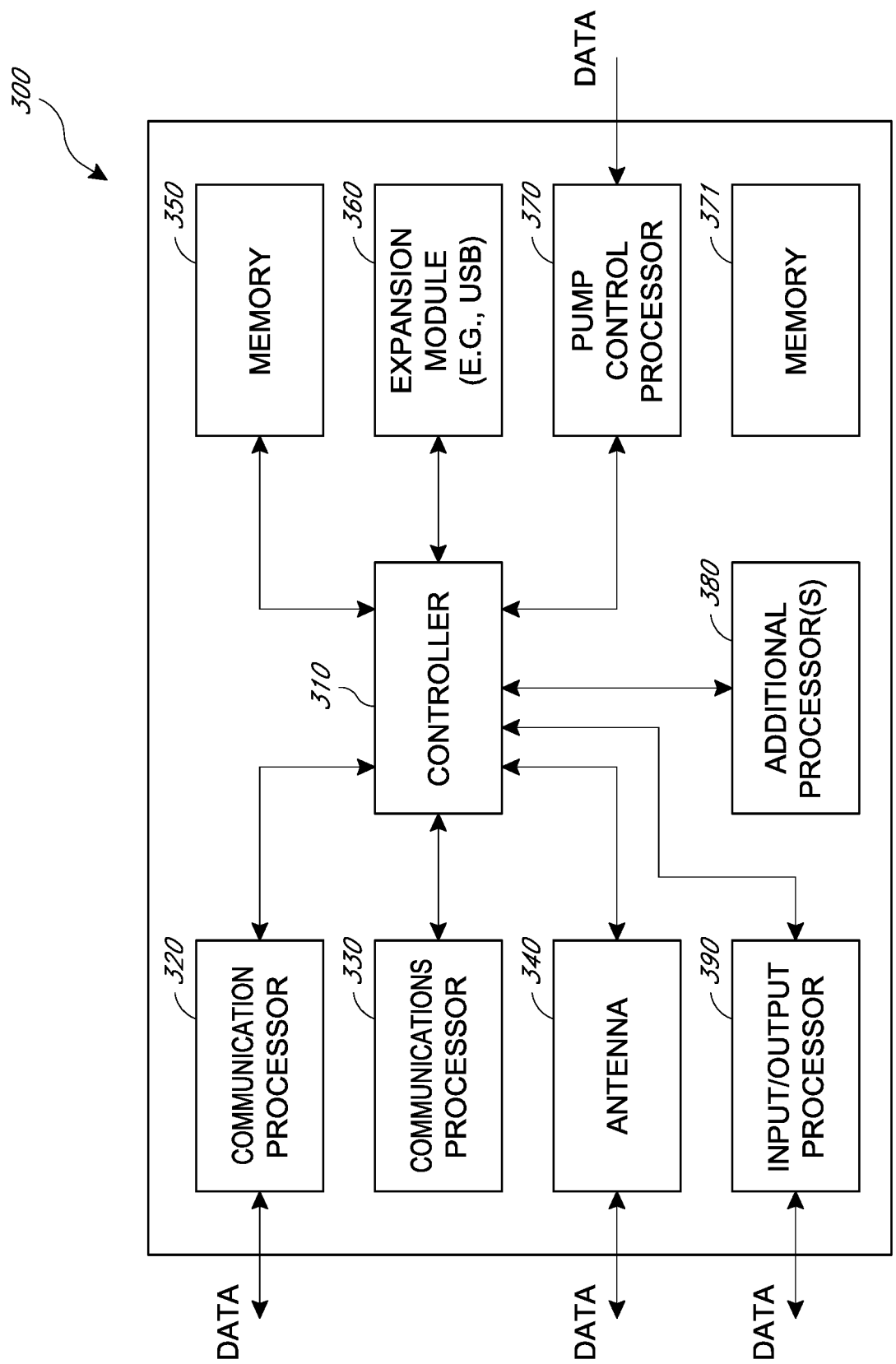
FIG. 3 illustrates an electrical component schematic of a negative pressure therapy apparatus according to some examples.

FIG. 3 illustrates an electrical component schematic 300 of the negative pressure therapy apparatus 220 according to some examples. Electrical components can operate to accept user input, provide output to the user, operate the pump assembly of the negative pressure therapy apparatus, provide network connectivity, and so on. Electrical components can be mounted on one or more PCBs. As is illustrated, the negative pressure therapy apparatus 220 can include multiple processors. It may be advantageous to utilize multiple processors in order to allocate or assign various tasks to different processors.

The negative pressure therapy apparatus 220 can comprise a user interface processor or controller 310 configured to operate one or more components for accepting user input and providing output to a user, such as the display, buttons, etc. Input to and output from the negative pressure therapy apparatus 220 can be controlled by an input/output (I/O) processor 390. For example, the I/O processor 390 can receive data from one or more ports, such as serial, parallel, hybrid ports, and the like. The controller 310 can receive data from and provide data to one or more expansion module 360, such as one or more USB ports, SD ports, Compact Disc drives, DVD drives, FireWire ports, Thunderbolt ports, PCI Express ports, and the like.

The controller 310, along with other controllers or processors 380, can store data in one or more memory 350, which can be internal and/or external to the controller 310. Any suitable type of memory can be used, including volatile and/or non-volatile memory, such as RAM, ROM, magnetic memory, solid-state memory, magnetoresistive random-access memory (MRAM), and the like.

The controller 310 can be a general purpose controller, such as a low-power processor. In other instances, the controller 310 can be an application specific processor. Still, in other examples, the controller 310 can be configured as a "central" processor in the electronic architecture of the negative pressure therapy apparatus 220, and the controller 310 can coordinate the activity of other processors, such as a pump control processor 370, communications processor 330, and one or more additional processors 380. The controller 310 can run a suitable operating system, such as a Linux, Windows CE, VxWorks, etc.

A pump control processor 370 can be configured to control the operation of a negative pressure source of the negative pressure therapy apparatus. The pump control processor can control the level of negative pressure which can be pressure set or selected by a user. The negative pressure source can be a suitable pump, such as a diaphragm pump, peristaltic pump, rotary pump, rotary vane pump, scroll pump, screw pump, liquid ring pump, diaphragm pump operated by a piezoelectric transducer, voice coil pump, and the like.

In some cases, one or more of processors described herein in connection with FIG. 3 other than the controller 310 are not used, and the controller 310 performs one or more tasks of such omitted one or more processors. In some embodiments, the controller 310 is the only processor of the negative pressure therapy apparatus 220, and the controller 310 performs one or more tasks of the other processors described herein.

The negative pressure therapy apparatus 220 can be configured to communicate with at least one WCD 210. For example, the negative pressure therapy apparatus 220 can include a communication processor 320 configured to wirelessly communicate with a WCD 210. The wireless communication processor 320 can be configured to provide wireless communication over wireless networks (such as Wi-Fi internet networks, Bluetooth networks, etc.), over telecommunications networks (such as 3G networks, 4G networks, etc.), or over any other suitable wireless connection.

The communication processor 320 can be a transceiver or a receiver configured to receive one or more request signals from a WCD. For instance, the negative pressure therapy apparatus 220 can be interrogated by a WCD 210. In this aspect, the negative pressure therapy apparatus 220 is responsive to the interrogation by sending a response reflecting operating data. In some examples, the communication processor 320 can be a transceiver or a one-way transmitter configured to transmit one or more signals based at least in part on one or more operating data.

The communication processor 320 can be a transceiver that, for instance, handshakes with at least one WCD 210 to communicate data from the negative pressure therapy apparatus to a WCD 210. Accordingly, the negative pressure therapy apparatus 220 can respond to data requests from at least one WCD 210. In still another aspect, a negative pressure therapy apparatus 220 can reflect or redirect event or operating data to at least one WCD 210 in response to a WCD 210 radiating a negative pressure therapy apparatus 220 with transponder frequencies.

The communications processor 320 can include a transceiver. The negative pressure therapy apparatus 220 can be configured to listen for interrogating signals from the WCD 210 and, in turn, can relay event or operating data from the negative pressure therapy apparatus 220 to the WCD 210. Alternatively, the negative pressure therapy apparatus 220 can relay event or operating data at set time intervals or when the negative pressure therapy apparatus 220 accumulates data close to an internal storage limit.

The negative pressure therapy apparatus 220 can include internal memory 350 and can store one or more event or operating data in the memory 350. When the memory 250 is nearly full, the negative pressure therapy apparatus 220 can transmit the stored data wirelessly to a WCD 210. In some embodiments, stored data is transmitted to a WCD 210 in response to receiving a request and/or occurrence of a triggering condition. In some implementations, the negative pressure therapy apparatus 220 can periodically transmit stored data. Other transmission protocols can be used without departing from the scope of this disclosure.

Communication processor 320 can be a secure communications port. By way of example, a negative pressure therapy apparatus 220 can release internal data only to a WCD 210 with the correct passwords and/or data protocols. In another example, the communication processor 320 can be an infrared communications port. Such a port, in one aspect, can be configured to communicate with at least one WCD in secure communication protocols.

In some cases, the negative pressure therapy apparatus 220 does not include a user interface (i.e., display screen, buttons, etc.). In these instances, the communication processor 320 can be a receiver or transceiver configured to receive instructions, user input, or other data from at least one WCD 210. In some instances, a negative pressure therapy apparatus 220 can include a limited set of user input components (such as an on/off button, Bluetooth pairing, etc.).

FIG. 4 illustrates an electrical component schematic 400 of the WCD 210 according to some examples. As shown, the WCD 210 can comprise a user interface processor or controller 411 configured to operate one or more components configured to accept user input (such as touch screen display, keyboard, button(s), voice command, etc.), transmit operating data requests or operation instructions (such as pump control, negative pressure selection, etc.), receive one or more signals representing operating data, provide output to a user (such as via a display, indication, signal and/or alarm), provide network connectivity, and so on.

Input to and output from a WCD 210 can be controlled by an input/output (I/O) processor 461. For example, the I/O processor can receive data from one or more ports, such as serial, parallel, hybrid ports, and the like. The controller 411, along with other controllers or processors, can store data in one or more memory 451, which can be internal and/or external to the controller 411. Any suitable type of memory can be used, including volatile and/or non-volatile memory, such as RAM, ROM, magnetic memory, solid-state memory, Magnetoresistive random-access memory (MRAM), and the like.

A communications processor 431 can be configured to provide wired and/or wireless connectivity. The communications processor 431 can utilize one or more antenna(s) 441 for sending and receiving. In some embodiments, the communications processor 431 can provide one or more of the following types of connections: Global Positioning System (GPS) technology, cellular connectivity (such as 2G, 3G, LTE, and 4G), Wi-Fi connectivity, Internet connectivity, Bluetooth connectivity, and the like.

The communication processor 421 can be a one-way receiver configured to receive signals (for instance, signals representing operating data) from a negative pressure therapy apparatus 220. As mentioned above, operating data can include information related to power status data, error data, negative pressure data, dressing data, connection data, activity logs, patient data and the like.

The communication processor 421 can be a transceiver configured to both transmit requests to and receive responses from a negative pressure therapy apparatus 220. For instance, by integrating a transceiver and antenna with a processing section, the WCD 210 can interrogate negative pressure therapy apparatus for operating data information. In this way, users of the WCD 210 can learn of the negative pressure therapy apparatus operating data at any desired time. In one example, the WCD 210 can receive input from a user, wherein the user is requesting one of more operating data. The WCD 210 can generate a request based at least in part on the user input and transmit the request to a negative pressure therapy apparatus 220. Thereafter, the WCD 210 can receive a response from the negative pressure therapy apparatus 220, from which the WCD 210 can interpret the one or more operating data requested by the user.

A WCD 210 can transmit control instructions to the negative pressure therapy apparatus. For instance, by sending control instructions, a user can use the WCD 210 to control the pump, adjust the level of negative pressure, toggle the power of the negative pressure therapy apparatus, and the like.

The communication processor 421 can be a transceiver that handshakes with a negative pressure therapy apparatus 220 to communicate. Accordingly, a WCD 210 can transmit data requests to at least one negative pressure therapy apparatus 220. In still another aspect, the WCD 210 can "radiate" the negative pressure therapy apparatus 220 with transponder frequencies and, in response, the negative pressure therapy apparatus 220 can "reflect" event or operating data to a WCD.

The WCD 210 can include a receiver 421 from which it can communicate externally to the negative pressure therapy apparatus 220. The WCD 210 can listen for data from the negative pressure therapy apparatus 220 and collect that data for subsequent relay or use. In some aspects, the WCD can receive operating data (a) in response to its request; (b) upon the occurrence of an event (such as a detected error); or (c) in repeated time intervals, (such as once every ten minutes, thirty minutes, 2 hours, 4 hours, etc.).

The WCD 210 can be utilized to perform one or more of the following: initialization and programming of the negative pressure therapy apparatus 220, firmware and/or software upgrades, maintenance and troubleshooting, selecting and adjusting therapy parameters, and the like.

In some cases, one or more of processors described herein in connection with FIG. 4 other than the controller 411 are not used, and the controller 411 performs one or more tasks of such omitted one or more processors. In some embodiments, the controller 411 is the only processor in the WCD 210, and the controller 411 performs one or more tasks of the other processors described herein.

Terminology

Depending on the embodiment, certain operations, acts, events, or functions of any of the processes described herein can be performed in a different sequence, can be added, merged, or left out altogether (such as not all are necessary for the practice of the processes). Moreover, in certain embodiments, operations, acts, functions, or events can be performed concurrently, such as through multi-threaded processing, interrupt processing, or multiple processors or processor cores or on other parallel architectures, rather than sequentially.

Systems and processors described herein may comprise software, firmware, hardware, or any combination(s) of software, firmware, or hardware suitable for the purposes described herein. Software and/or firmware may be stored on non-transitory computer readable media. Software and other processors may reside and execute on servers, workstations, personal computers, computerized tablets, PDAs, and other computing devices suitable for the purposes described herein. Software and other processors may be accessible via local memory, via a network, via a browser, or via other means suitable for the purposes described herein. Data structures described herein may comprise computer files, variables, programming arrays, programming structures, or any electronic information storage schemes or methods, or any combinations thereof, suitable for the purposes described herein. User interface elements described herein may comprise elements from graphical user interfaces, interactive voice response, command line interfaces, and other suitable interfaces.

Further, the processing of the various components of the illustrated systems can be distributed across multiple machines, networks, and other computing resources. In addition, two or more components of a system can be combined into fewer components. Various components of the illustrated systems can be implemented in one or more virtual machines, rather than in dedicated computer hardware systems and/or computing devices. Likewise, the data repositories shown can represent physical and/or logical data storage, including, for example, storage area networks or other distributed storage systems. Moreover, in some embodiments the connections between the components shown represent possible paths of data flow, rather than actual connections between hardware. While some examples of possible connections are shown, any of the subset of the components shown can communicate with any other subset of components in various implementations.

Any patents and applications and other references noted above, including any that may be listed in accompanying filing papers, are incorporated herein by reference. Aspects of the disclosure can be modified, if necessary, to employ the systems, functions, and concepts of the various references described herein to provide yet further implementations.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Likewise the term "and/or" in reference to a list of two or more items, covers all of the following interpretations of the word: any one of the items in the list, all of the items in the list, and any combination of the items in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the description of certain embodiments and may be defined by the claims. The language of the claims is to be interpreted broadly based on the language employed in the claims and not limited to the examples described in the present specification or during the prosecution of the application, which examples are to be construed as non-exclusive.

What is claimed is:

1. A negative pressure wound therapy system comprising:
a negative pressure therapy apparatus configured to apply negative pressure to a wound of a patient, the negative pressure therapy apparatus comprising:
a wound dressing configured to be placed over the wound, a negative pressure source embedded in the wound dressing and configured to apply negative pressure to the wound, and
a first controller configured to determine operating data of the negative pressure therapy apparatus;
a first wireless communication device configured to be communicatively coupled to the negative pressure therapy apparatus, the first wireless communication device comprising:
a first display,
a second controller configured to receive the operating data from the negative pressure therapy apparatus and output an indication of at least some of the operating data on the first display, and
a first wearable housing configured to support the first display and the second controller of the first wireless communication device, wherein the first wearable housing is configured to be worn by the patient or a caregiver of the patient;
a second wireless communication device configured to be communicatively coupled to the negative pressure therapy apparatus, the second wireless communication device comprising:
a second display,
a third controller configured to receive the operating data from the negative pressure therapy apparatus and output an indication of at least some of the operating data on the second display, and
a second wearable housing configured to support the second display and the third controller of the second wireless communication device, wherein the second wearable housing is configured to be worn by the patient or the caregiver of the patient,
wherein the second controller of the first wireless communication device is configured to handover communication with the negative pressure therapy apparatus to the third controller of the second wireless communication device,
wherein the handover causes the operating data to be received by the third controller of the second wireless communication device but not by the second controller of the first wireless communication device;
wherein the first wireless communication device and the second wireless communication device are configured to transmit a user input to the first controller, and the first controller is configured to receive the user input from at least one of the first wireless communication device and the second wireless communication device; and
wherein the negative pressure therapy apparatus is further configured to transmit the operating data to one or both of the first and second wireless communication devices responsive to an expiration of a time interval.

2. The system of claim 1, wherein the operating data comprises at least one of a power status of the negative pressure therapy apparatus, error data associated with the negative pressure therapy apparatus, connection data corresponding to communications between the negative pressure therapy apparatus and one or both of the first and second wireless communication devices, negative pressure data associated with the negative pressure source, wound data associated with the wound, dressing data, activity data, or patient data.

3. The system of claim 1, wherein the wound is located in an area that is remote from the first wearable housing.

4. The system of claim 3, wherein the area includes at least one of a back, a shoulder, a leg, a hip, a foot, or a buttocks of the patient.

5. The system of claim 3, wherein the area includes at least a portion of the patient's posterior.

6. The system of claim 1, wherein the negative pressure therapy apparatus is a first negative pressure therapy apparatus, the wound dressing is a first wound dressing, the negative pressure source is a first negative pressure source, the wound is a first wound, and the operating data is first operating data, the system further comprising:
a second negative pressure therapy apparatus to apply negative pressure to a second wound of the patient, the second negative pressure therapy apparatus comprising:
a second wound dressing configured to be placed over the second wound,
a second negative pressure source supported by the second wound dressing and configured to apply negative pressure to the second wound, and
a fourth controller configured to determine second operating data of the second negative pressure therapy apparatus,
wherein one or both of the first and second wireless communication devices is communicatively coupled to the second negative pressure therapy apparatus and is further configured to:
receive the second operating data from the second negative pressure therapy apparatus, and
output an indication of at least some of the second operating data on the display.

7. The system of claim 6, wherein the second controller is further configured to:
generate a first request for the first operating data;
generate a second request for the second operating data; and
communicate the first and second requests to the first and second negative pressure therapy apparatuses, respectively.

8. The system of claim 7, wherein the first controller is further configured to transmit the first operating data to one or both of the first and second wireless communication devices responsive to receipt of the first request, wherein the fourth controller is further configured to transmit the second operating data to one or both of the first and second wireless communication devices responsive to receipt of the second request.

9. The system of claim 1, wherein at least one of the first and second wearable housings are sized to be worn on a wrist.

10. The system of claim 1, wherein the handover occurs responsive to a determination that a first connection between the first wireless communication device and the negative pressure wound therapy apparatus is less reliable than a second connection between the second wireless communication device and the negative pressure wound therapy apparatus.

11. The system of claim 10, wherein the determination that the first connection between the first wireless communication device and the negative pressure wound therapy apparatus is less reliable than the second connection between the second wireless communication device is made based on the second wireless communication device being located closer to the negative pressure wound therapy apparatus than the first wireless communication device.

12. The system of claim 1, wherein the handover occurs responsive to a determination that the second wireless communication device is located closer to the negative pressure wound therapy apparatus than the first wireless communication device.

13. The system of claim 1, wherein only one of the first and second wireless communication devices is configured to generate and transmit a request for the operating data of the negative pressure therapy apparatus.

14. The system of claim 1, wherein the first wireless communication device and the second wireless communication device are configured to directly transmit a user input to the first controller, and the first controller is configured to receive the user input directly from at least one of the first wireless communication device and the second wireless communication device.

15. The system of claim 1, wherein the operating data comprises error data associated with the negative pressure therapy apparatus.

* * * * *